United States Patent [19]
Roos

[11] Patent Number: 5,014,877
[45] Date of Patent: May 14, 1991

[54] PELLET DISPENSER
[75] Inventor: William N. Roos, Colgate, Wis.
[73] Assignee: Autotrol Corporation, Milwaukee, Wis.
[21] Appl. No.: 429,263
[22] Filed: Oct. 30, 1989
[51] Int. Cl.⁵ .............................................. B65G 59/00
[52] U.S. Cl. ................................... 221/265; 221/203; 221/258; 221/263
[58] Field of Search ................. 221/97, 101, 203, 258, 221/263, 264, 265, 266, 277, 311, 312; 222/200, 370, 362

[56] References Cited
U.S. PATENT DOCUMENTS

| | | |
|---|---|---|
| 736,257 | 8/1903 | Heylman . |
| 1,562,152 | 11/1925 | Dy Gremier . |
| 1,651,605 | 12/1927 | Kuhn et al. ........................ 221/203 |
| 1,884,365 | 10/1932 | Suppiger et al. ............... 221/265 X |
| 2,649,994 | 8/1953 | Lewis et al. . |
| 3,232,621 | 2/1966 | Michelson . |
| 3,253,738 | 5/1966 | Bromley . |
| 3,706,396 | 12/1972 | Knapp et al. . |
| 3,730,387 | 5/1973 | McConnell et al. ................ 221/265 |
| 3,785,525 | 1/1974 | Handeland . |
| 3,885,703 | 5/1975 | Neavin ........................... 221/265 X |
| 3,991,908 | 11/1976 | Thomas et al. ................. 221/265 X |
| 4,150,766 | 4/1979 | Westendorf et al. . |
| 4,216,788 | 8/1980 | Watanabe et al. . |
| 4,235,849 | 11/1980 | Handeland . |
| 4,513,688 | 4/1985 | Fassauer ........................ 222/200 X |
| 4,662,538 | 5/1987 | Goudy, Jr. et al. . |

FOREIGN PATENT DOCUMENTS 0795644 10/1968 Canada .
1086632 2/1955 France .

Primary Examiner—Robert P. Olszewski
Assistant Examiner—Tuan N. Nguyen
Attorney, Agent, or Firm—Quarles & Brady

[57] ABSTRACT

A pellet dispensing device having a rotor member with a pellet passage for transporting a pellet to a discharge opening. The rotor member has an escapement groove at the bottom for pieces of the pellet to be accommodated so that they do not jam the full sized pellets in the pellet passage. In a preferred embodiment, there is an additional groove at the top of the rotor member and in communication with the pellet passage which allows full sized pellets to be ejected therefrom by a dam member.

8 Claims, 2 Drawing Sheets

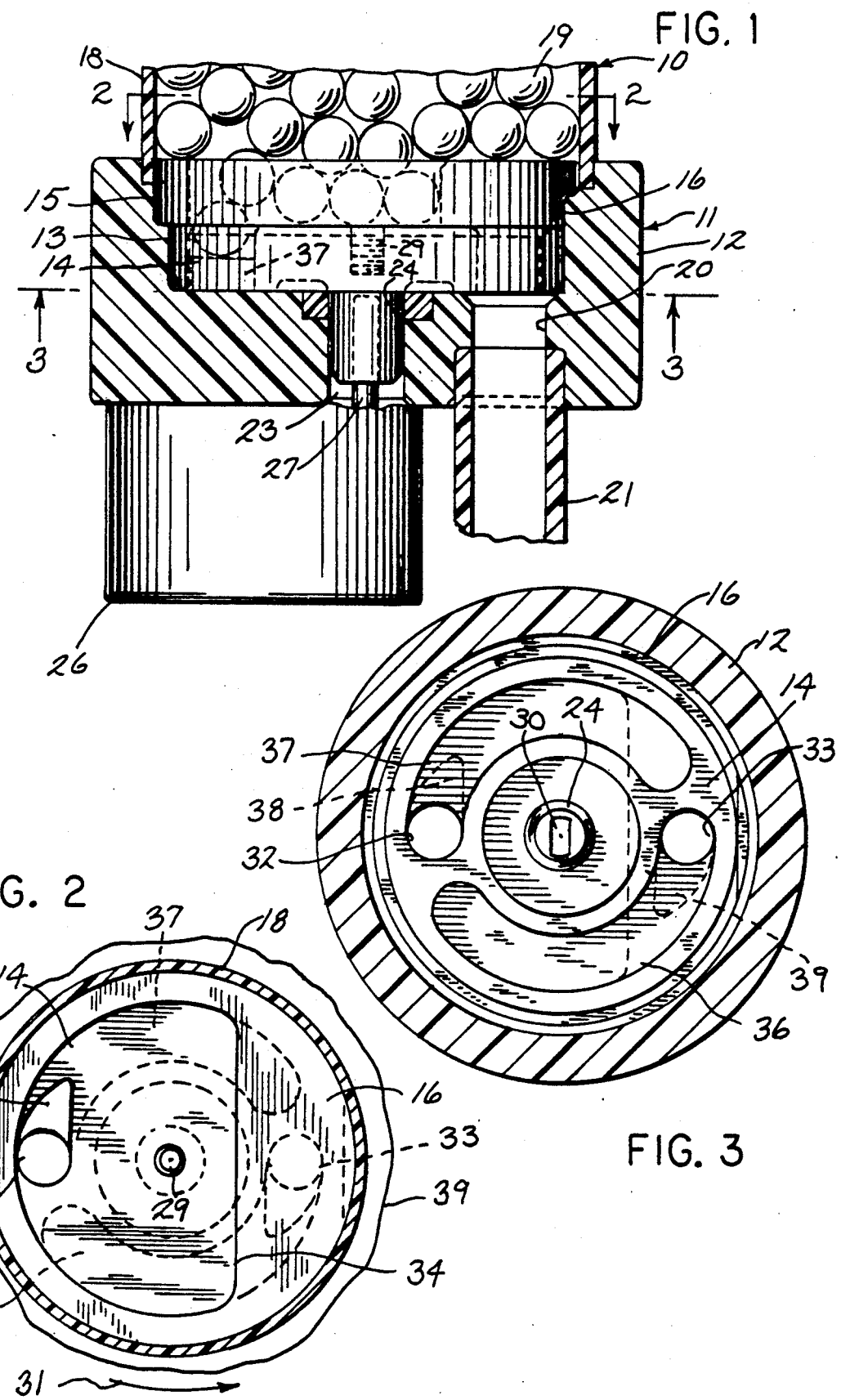

PELLET DISPENSER

BACKGROUND OF THE INVENTION

This invention relates to a pellet handling device which can dispense pellets from a bulk supply source without the pellets becoming jammed therein. More particularly, it relates to a pellet dispensing apparatus which employs a unique pellet plate or rotor member so that it can accommodate pieces of the tablet thereby preventing the pieces from becoming jammed with the pellets as the pellet plate rotates to dispense them through a discharge passage.

Chemical pellet dispensing devices of the type concerned with in this invention are disclosed in U.S. Pat. Nos. 3,785,525; 4,235,849; and 4,662,538, the latter patent being commonly assigned. The use of a metering or pellet plate for presenting pellets through an aperture in a base plate is commonly used in this particular art. U.S. Pat. Nos. 3,785,525 and 4,235,849 are representative of these types of apparatus. The use of the rotating metering plate poses problems as pieces of pellets can become lodged with full-sized pellets in the metering plate orifice and thus can cause a jamming of the pellets. In U.S. Pat. No. 4,662,538 a specially designed rotor assembly is presented which in effect carries the pellet over the floor of the base plate thus reducing the risk of tablet pieces from becoming jammed in the rotating metering plate.

It is an advantage of the present invention to provide a pellet dispensing apparatus which reduces the incidence of pellets becoming jammed in the pellet dispenser.

It is another advantage of this invention to provide a pellet dispensing apparatus which not only can accommodate broken pieces of tablet but also assures that only a single pellet is dispensed from a pellet carrying passage.

Still another advantage of this invention is a pellet dispensing apparatus which has a few number of parts and can be accommodated in various types of pellet dispensing apparatus.

It is yet another advantage of this invention to provide a pellet dispensing apparatus in which the components are easily moldable from plastic materials and thus is cost effective.

Other advantages of this invention are a pellet dispensing apparatus wherein the pellet plate can have various numbers and sizes of pellet passages, will allow for a second pellet to be ejected from the pellet plate and can be used with various containers for the pellets.

SUMMARY OF THE INVENTION

The foregoing advantages are accomplished and the shortcomings of the prior art are overcome by the present dispensing device. The dispensing device is operable with a container means having a wall portion with an opening. A pellet discharge means in the form of a discharge tube is connected to a rotor assembly which is connected to a hopper wall opening. The rotor assembly includes a pellet plate or a rotor member having at least one pellet carrying passage. The pellet carrying passage is in communication with the container wall opening and in a selected position is in communication with the pellet discharge means. A dam means is positioned above the rotor member to eject excess pellets out of the pellet carrying passage. A drive means is operatively associated with the rotor member to rotate said rotor member. The pellet discharge means is positioned adjacent the bottom of the rotor assembly when mounted in connection with the container means. The rotor member includes escapement means in connection with the pellet carrying passage to permit smaller than average size pellets or pieces to enter when the rotor member is moved toward the pellet discharge means.

In a preferred embodiment, the escapement means is defined by a groove member having a depth smaller than the average largest dimension of the pellets.

In one aspect of the invention, there is the foregoing described rotor assembly with the escapement means which is adapted to receive a pellet container wall at one side and the discharge means and the drive means at the other side.

In another aspect of the invention, there is presented a three component dispensing device for pellets which includes a rotor housing adapted to receive a pellet container wall with the rotor housing also including a pellet discharge means. A rotor member is disposed in the rotor housing having at least one pellet carrying passage. The pellet carrying passage is in communication with a container wall opening and in a selected position is in communication with the pellet discharge means, the rotor member having groove portions in lateral communication with both ends of the pellet carrying passage and at the same side thereof. A dam member is positioned above the rotor member to prevent pellets from entering directly into said pellet carrying passage. The rotor member is connectable to a drive means to rotate the rotor members.

BRIEF DESCRIPTION OF THE DRAWINGS

A better understanding of the present pellet dispensing device will be accomplished by reference to the drawings wherein:

FIG. 1 is a view in partial vertical section illustrating the pellet dispenser of this invention.

FIG. 2 is a view in horizontal section taken along line 2—2 of FIG. 1.

FIG. 3 is a view in horizontal section taken along line 3—3 of FIG. 1.

DESCRIPTION OF THE EMBODIMENTS OF THE INVENTION

Figure 4:
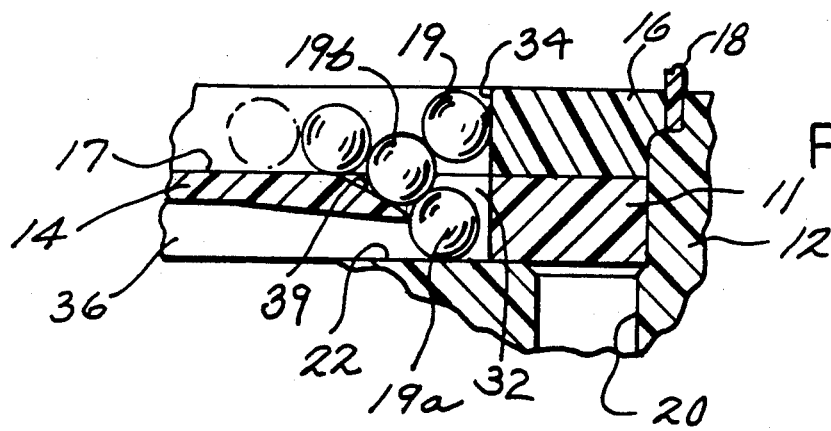
FIGS. 4–7 are partial views in vertical section illustrating the movement of the pellets through the pellet dispenser and with respect to FIGS. 6 and 7 in particular showing the movement of a partial pellet.

Proceeding to a detailed description of the embodiments of the present invention and particularly to FIG. 1, the pellet dispenser generally 10 includes a rotor assembly 11 generally having a housing 12 with a cavity 13 for accommodating a rotor member or pellet plate 14. Housing 12 also has an enlarged cavity section 15 for accommodating a dam member 16 above the rotor member 14. A container 18 for the pellets 19 is secured to the housing 12 and has an open end for depositing the pellets therein. At the opposing end of the housing 12 there is a pellet discharge passage 20 to which is secured a pellet discharge tube 21.

A stem portion 24 extends from the rotor member 14 and is positioned in a central cavity or opening 23 and is guided by the bearing washer 25. A motor 26, preferably of the electric type, is suitably fastened to the housing 12 and has a drive shaft 27 fastened to the stem 24. As best seen in FIG. 3, there is the slot 30 in the stem portion 24 for receiving the drive shaft 27 in a nonrotating engagement.

As best seen in FIG. 2, there are two pellet passages 32 and 33 which extend completely through the rotor member 14. There are in addition tapered wall sections 38 and 39 which communicate laterally with the pellet passages 32 and 33. As indicated in FIG. 2, by the directional arrow 31, the rotation of the rotor member 14 is in a counterclockwise manner. Accordingly, the tapered walls 38 and 39 communicate with the pellet passages 32 and 33 on the backside of the passages and taper in a narrowing manner away from the pellet passages.

Referring to FIG. 3, it is seen that there are two arcuate grooves 36 and 37 communicating laterally with the pellet passages 33 and 32, respectively. The purpose of these arcuate grooves 36 and 37 as well as the tapering wall portions 38 and 39 will best be understood in conjunction with the following operation.

OPERATION

Figure 5:
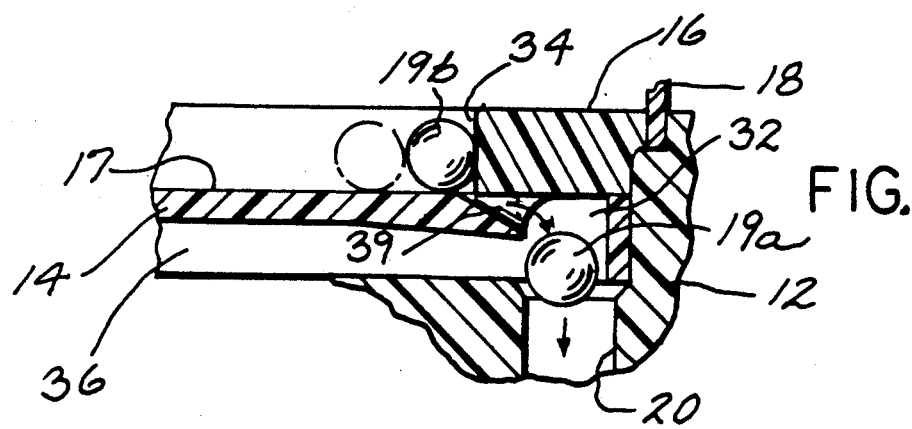

A better understanding of the advantages of the pellet dispenser 10 will be by a description of its operation. This is best illustrated in conjunction with FIGS. 4–7. Referring first to FIG. 4, the pellets such as 19 are delivered to the upper surface 17 of the rotor member 14 from the container 18. It will be appreciated that the pellet dispenser 10 operates in the most efficient manner when the pellet dispenser 10 and the container 18 are in an upright manner with the container 18 in a vertical position and the rotor member 14 perpendicular with gravitational forces. The pellets are free to flow onto and across the surface 17 where they will seek to fill the pellet passages 32 and 33. These passages are designed so that only one pellet, such as 19a, can move through the passage 32 and will do so until it contacts the upper surface 22 of the housing 12. This is best seen by the pellet 19a in FIG. 4. Other pellets will also attempt to fill the passage as indicated by the pellet 19b resting on the tapered wall 39 leading into the pellet passage 32. It will be appreciated that the dam member 16 is positioned over the pellet discharge passage 20 so that no pellets will pass directly into the discharge passage. The motor 26 through the drive shaft 27 rotates the rotor member 14 in a manner so as to position the passage 32 with the pellet 19a over the discharge opening 20. This is best seen in conjunction with FIG. 5 where the pellet 19a is now positioned so as to drop through the pellet discharge opening 20 and out through the discharge tube 21. Before doing so it should be recognized in conjunction with FIGS. 4 and 5 that the pellet 19b, which previously was in the tapered wall portion 39, has been moved therefrom and is now positioned back on the surface 17. This is effected through the contact of the wall 34 of the dam 16 which engages the pellet 19b and moves it upwardly over the tapered wall 39 until it is positioned as seen in FIG. 5. This pellet will then remain in this position as the rotor member 14 passes under the dam member 16.

Figure 6:
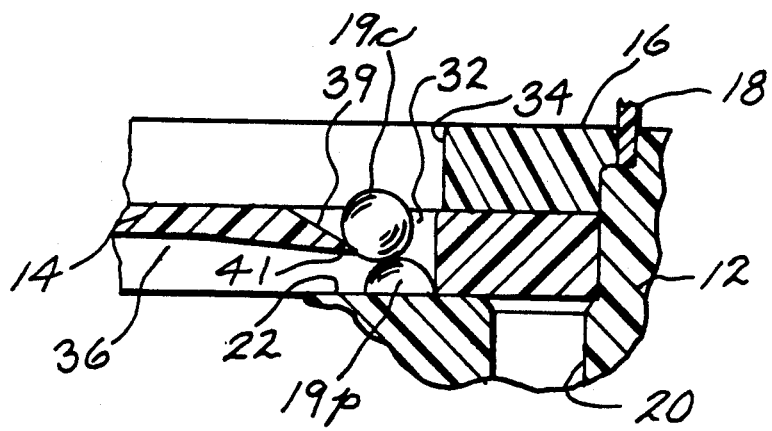
Figure 7:
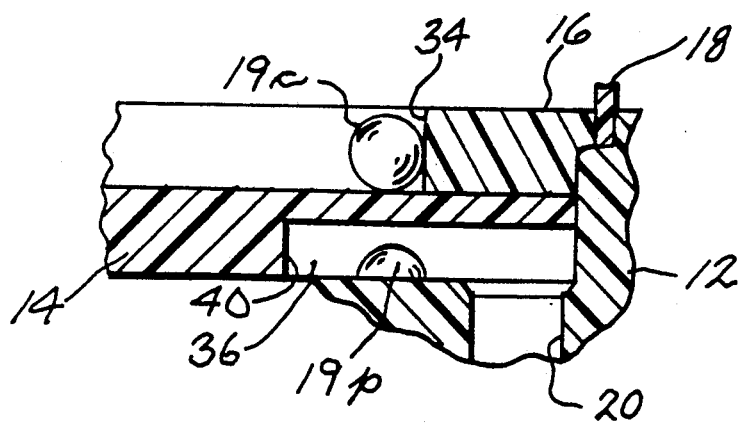

FIGS. 6 and 7 illustrate the functioning of the pellet dispenser when a piece of a pellet such as indicated at 19p is present. It will be recognized that in many instances there are pieces of the pellets intermixed with the pellets. This causes problems in that the pieces of the pellet and a whole pellet can become jammed in the pellet discharge passage such as 32 if this passage were to be a straight wall structure through the rotor member 14. In order to avoid this problem, there are provided the groove members 36 and 37 in the rotor member 14 which are of a sufficient dimension and extend above the surface 22 of the housing 12 so as to accommodate a piece of pellet such as 19p but yet not except a full pellet such as 19c. This is best seen in conjunction with the groove member 36 and the distance between the surface 22 and the lowest most portion of the groove as indicated by the wall surface 41. As the rotor member 14 rotates in the direction of the pellet discharge passage 20, the pellet piece 19p, because of its reduced height, will pass under the wall surface 41 remaining in a somewhat stationary position on the surface 22 until it is contacted by the moving wall 40 at the end of the groove 36. Contact with this wall will then move the pellet piece 19p down the pellet discharge passage 20 and ultimately out through the pellet discharge tube 21.

In a preferred manner, there are two pellet passages 32 and 33 and groove members 36 and 37 in the rotor member 14. Obviously, any number of such passages and grooves could be employed depending upon the size of pellets to be accommodated and the size of the rotor member. Their number could also be reduced to one if desired. The tapered walls 38 and 39 have been shown in conjunction with the pellet passages 32 and 33. While these aid in moving an undesired pellet from the pellet passages 32 and 33, the benefits of accommodating the pellet pieces under the rotor member with the grooves 36 and 37 could still be accomplished without them although some slight chamfering of the wall surface surrounding the passage would be desired depending upon the configurations of the pellets.

It is noted in conjunction with FIGS. 4–7 that the bottom wall 41 of the rotor member 14 forming the groove 36 tapers downwardly toward the surface 22 of the housing 12. This tapering is not essential but was done in this instance to accomplish the molding of the rotor member 14. Further a screw 29 is shown connected to the rotor member 14. This is not essential and is shown for the purpose of providing a means for easily removing the rotor member for maintenance purposes.

The rotor member 14, the dam member 16 as well as the housing 12 are all injection molded from a rigid polyurethane plastic material. This lends itself to an assembly which is not easily corrodible where corrosive pellet materials are being dispensed. Further, it should be noted that the pellet dispenser is simple in its construction and composed of basically three elements which is the rotor member 14, the dam member 16 and the housing 12. This provides a simplified structure as well as one which is highly reliable and easy to maintain.

The pellet dispenser of this invention is capable of dispensing pellets or tablets of various geometric configurations and compositions. In this instance, the pellet dispenser is designed for use in dispensing tablets into a well casing for water treatment. The pellet dispenser of this invention is just as easily operable in conjunction with other water treatment systems such as a large or small scale water cooling tower for an air conditioning system. It could also be used in conjunction with other facilities which would require the sequential placement of a pellet or tablet in the system such as in waste water treatment or food processing.

The foregoing invention can now be practiced by those skilled in the art. Such skilled persons will know that the invention is not necessarily restricted to the particular embodiments presented herein but the scope of the invention is to be defined by the terms of the following claims as given meaning by the preceding description.

I claim:

1. A dispensing device for pellets comprising:
   a container means having a wall portion with an opening;
   a pellet discharge means;
   a rotor assembly operatively connected with said container wall opening and said pellet discharge means, said rotor assembly including a rotor member having at least one pellet carrying passage, said pellet carrying passage having a pellet entry portion and a pellet exit portion, said pellet carrying passage being in communication with said container wall opening and in a selected position being in communication with said pellet discharge means;
   dam means positioned above said rotor member to eject excess pellets out of said pellet carrying passage;
   drive means operatively associated with said rotor member to rotate said rotor member;
   wherein said pellet discharge means is positioned adjacent the bottom of said rotor assembly when mounted in connection with the container means; and
   wherein said rotor member includes escapement means in communication with said exit portion of said pellet carrying passage to permit smaller than average size pellets to enter when said rotor member is moved toward said pellet discharge means.

2. The dispensing device of claim 1 wherein said escapement means is defined by a groove member having a depth smaller than the average largest dimension of said pellets.

3. The dispensing device of claim 2 wherein said groove member is defined by a sloping wall portion which tapers in a narrowing manner in the direction of said pellet carrying discharge passage.

4. The dispensing device of claim 2 wherein said escapement means is defined by two opposing accurate groove members.

5. The dispensing device of claim 1 further including a sloping wall which tapers in a narrowing manner away from said pellet carrying passages as they are rotated in said rotor assembly.

6. The dispensing device of claim 1 wherein said dam means is positioned over said pellet discharge means.

7. A rotor assembly for a pellet dispensing device comprising:
   a rotor housing adapted to receive a pellet container wall, said rotor housing also including a pellet discharge means;
   a rotor member disposed in said rotor housing having at least one pellet carrying passage, said pellet carrying passage having a pellet entry portion and a pellet exit portion, said pellet carrying passage being in communication with said container wall opening and in a selected position being in communication with said pellet discharge means, said rotor member adopted to be driven by a drive means;
   dam means positioned above said rotor member to eject excess pellets out of said pellet carrying passage;
   wherein said pellet discharge means is positioned adjacent the bottom of said rotor assembly when mounted in connection with said container means; and
   wherein said rotor member includes escapement means in communication with said exit portion of said pellet carrying passage to permit smaller than average size pellets to enter when said rotor member is moved toward said pellet discharge means.

8. A three component dispensing device for pellets comprising:
   a rotor housing adapted to receive a pellet container wall, said rotor housing also including a pellet discharge means;
   a rotor member disposed in said rotor housing having at least one pellet carry passage, said pellet carrying passage having a pellet entry portion and a pellet exit portion, said pellet carrying passage being in communication with said container wall opening and in a selected position being in communication with said pellet discharge means, said rotor member having groove portions in lateral communication with said pellet entry and exit portions and at the same side of said pellet carrying passage, said rotor member also adopted to be driven by drive means; and
   a dam member positioned above said rotor member to eject excess pellets out of said pellet carrying passage;
   wherein said pellet discharge means is positioned adjacent the bottom of said rotor assembly when mounted in connection with the container means; and
   wherein said groove portions in communication with said exit portion of said pellet carrying passage provide escapement means to permit smaller than average size pellets to enter when said rotor member is moved toward said pellet discharge means.

* * * * *